United States Patent
Raber et al.

(10) Patent No.: US 10,434,084 B2
(45) Date of Patent: Oct. 8, 2019

(54) CANNABINOID BLENDS AND FORMULATIONS, RELATED METHODS

(71) Applicant: Scientific Holdings, LLC, Monrovia, CA (US)

(72) Inventors: Jeffrey Charles Raber, Pasadena, CA (US); Bradley J Douglass, Seattle, WA (US); Braden Doane, Bellevue, WA (US)

(73) Assignee: Scientific Holdings, LLC, Monrovia, CA (US)

( * ) Notice: Subject to any disclaimer, the term of this patent is extended or adjusted under 35 U.S.C. 154(b) by 0 days.

(21) Appl. No.: 15/826,203

(22) Filed: Nov. 29, 2017

(65) Prior Publication Data

US 2018/0147179 A1    May 31, 2018

Related U.S. Application Data

(60) Provisional application No. 62/427,697, filed on Nov. 29, 2016.

(51) Int. Cl.
*A61K 31/352* (2006.01)
*A61K 9/00* (2006.01)
*A61K 36/185* (2006.01)
*A61K 9/16* (2006.01)

(52) U.S. Cl.
CPC .......... *A61K 31/352* (2013.01); *A61K 9/0056* (2013.01); *A61K 9/1676* (2013.01); *A61K 9/1682* (2013.01); *A61K 36/185* (2013.01)

(58) Field of Classification Search
CPC .... A61K 31/352; A61K 47/6939; A61K 9/14; A61K 9/0056; A61K 9/1676; A61K 9/1682; Y10T 428/2982
See application file for complete search history.

(56) References Cited

U.S. PATENT DOCUMENTS

| | | | | |
|---|---|---|---|---|
| 3,404,011 | A | * | 10/1968 | Eolkin ............... A23P 10/43 426/651 |
| 6,066,352 | A | * | 5/2000 | Ogasawara ............ A21D 2/26 426/549 |
| 2008/0193511 | A1 | * | 8/2008 | Massing ............... A61K 8/14 424/450 |
| 2014/0212517 | A1 | * | 7/2014 | Todosiev ............. B01D 1/00 424/725 |
| 2016/0243177 | A1 | * | 8/2016 | Franklin ............ A61K 36/185 |
| 2017/0274296 | A1 | * | 9/2017 | Todosiev ............. B01D 1/00 |

OTHER PUBLICATIONS

Burton, Jacob (How to "Dehydrate" Fat Using Tapioca Maltodextrin, Youtube video, https://www.youtube.com/watch?v=x5TToltpSUM, published in 2012) (Year: 2012).*

* cited by examiner

*Primary Examiner* — Mark V Stevens
(74) *Attorney, Agent, or Firm* — Patnstr, APC; Tom Brody; Peter Jon Gluck, Esq.

(57) ABSTRACT

The disclosure provides methods for making homogeneous powders that are enriched in cannabinoids, and for blending the mixtures with pigments, emulsifiers, or odorants. The powders can be based on carbohydrates, sugars, cellulose-based polymers, or proteins.

34 Claims, No Drawings

US 10,434,084 B2

CANNABINOID BLENDS AND FORMULATIONS, RELATED METHODS

CROSS REFERENCE TO RELATED APPLICATIONS

This application claims the benefit of, and priority to, U.S. Provisional Patent Application Ser. No. 62/427,697 filed Nov. 29, 2016, the content of which is incorporated herein by reference herein in its entirety.

BACKGROUND OF THE INVENTION

Particles taking the form of a powder can be used as a matrix for delivering compositions such as nutrients, food additives, flavors, fragrances, and medicines, where the compositions that are delivered reside in a coating on the particle. Various matrices can be coated, and these include sugar granules, small salt crystals, pellets of dried yeast, hard candies, and so on. Coated particles can be further processed into forms such as granules, tablets, or by applying additional coatings to create a multiply coated particle. Techniques for coating particles include spraying, such as spraying a solution or spraying a molten liquid, fluidized bed coating, and polymer coating (see, e.g., Teresk et al (2016) KONA Powder and Particle Journal. DO1:10.14356). Once manufactured, coated particles can be characterized by particle size analysis, scanning electron microscopy, or, by measuring specific surface area ([total surface area]/[unit of mass]) (Rawle A (2002) Adv. Colour Science Technol. 5:1-12). Examples of coated particles and methods for preparation are as follows. Particles of seasoning, flavoring, or protein, can be suspended in hot swirling air, and then sprayed with a coating of edible gum, wax, or resin (see, U.S. Pat. No. 3,949,096 of Johnson et al). Particles (0.015 mm) of cornstarch can be coated with a dye and, then coated with hydroxypropylcellulose, using a fluidized bed coater (see, e.g., Watano et al (204) Powder Technology. 141:172-176) To give another example, a chewable medicated tablet can be made from particles having ibuprofen and starch center, then coated with hydroxyethyl cellulose (see, U.S. Pat. No. 5,215,755 of Roche et al).

The present disclosure addresses the need for consumables taking the form of particles coated with cannabinoids. These compositions include powders and tablets, as well as dry instant mixes for making beverages.

DETAILED DESCRIPTIONS

As used herein, including the appended claims, the singular forms of words such as "a," "an," and "the" include their corresponding plural references unless the context clearly dictates otherwise. All references cited, herein are incorporated by reference to the same extent as if each individual patent, and published patent application, as well as figures, drawings, sequence listings, compact discs, and the like, was specifically and individually indicated to be incorporated by reference.

Cannabinoids

The present disclosure provides extracts, oils, slurries, suspensions, cooled viscous compositions, warmed viscous compositions, compositions comprising purified compounds optionally with one or more solvents, and the like, that comprise one or more of the following compounds; cannabinodiol; cannabichromene; cannabitriol; cannabidiol; cannabicyclol; cannabielsoin; cannabinodiol; cannabinol; delta8-tetrahydrocannabinol; delta9-tetrahydrocannabinol; cannabichromanone; cannabieoumaronone; cannabicitran; 10-oxo-delta6a10a-tetrahydrocannabinol; delta9-tetrabydrocannabivarin, cannabiglendol; delta7-isotetrahydrocannabinol; delta9-tetrahydrocannabinolic acid A and B; CBLVA; CBV; CBDV; CBEVA-B; CBCVA; CBDA; delta9-THCV A; CBDVA; CBGVA; divarinolic acid; quercetin; kaemferol; dihydrokaempferol; dihydroquerectin; cannflavin B; isovitexin; apigenin; naringenin; eriodictyol; luteolin; orientin; cytisoside; vitexin; canniprene; 3,4'-dihydroxy-5-methoxy bibenzyl; dihydroresveratrol; 3,4'dihydroxy-5,3'-dimethoxy-5'-isoprenyl; cannabistilbene 1; cannabistilbene 11a; cannabistilbene 11b; cannithrene 1; cannithrene 2; cannabispironc; iso-cannabispirone; cannabispirenon-A; cannabispirenone-B; cannabispiradierione; alpha-cannabispiranol; beta-cannabispiranol; acetyl-cannabispirol; 7-hydroxy-5-methoxyindan-1-spiro-cycyclohexane; 5-hydroxy-7-methoxyindan-1-spiro cyclohexane; myristic acid, palmitic acid, oleic acid, stearic acid, linoleic acid, linolenic acid, arachidic acid, eicosenoic acid, behenic acid, lignoceric acid, 5,7-dihydroxyindan-1-cyclohexane; cannabispiradienone: 3,4'-dihydroxy-5-methoxybibenzyl; canniprene; cannabispirone; cannithrene 1; cannithrene 2; alpha-cannabispiranol; acetyl-cannabisphirol; vomifoliol; dihydrovomifoliol; beta-ionone; dihydroactinidiolide; palustrine; palustridine; plus-cannabisativine; anhydrocannabisativine; dihydroperiphylline; cannabisin-A; cannabisin-B; cannabisin-C; cannabisin-D; grossamide; cannabisin-E; cannabisin-F; cannabisin-G; and so on See, e.g., Flores-Sanchez and Verpoorte (2008) Secondary metabolism in cannabis in Phytochem. Rev. DOI 10.1007/s1 1101-008-9094-4.

Terpenes

The founder ofterpene chemistry is Otto Wallach who received the Nobel Prize in 1910 (Christmann (2010) Angew Chem. Int. Ed. Engl. 49:9580-9586). The terpenes are biosynthesized from units of isoprene which can be linked to form linear chains or rings. In increasing length, the terpenes include hemiterpenes (single isoprenoid unit)), monoterpenes (two units), sesquiterpenes (three units), diterpenes (four units) sesterterpenes (five units), triterpenes (six units), and so on. Non-aromatic terpenes include vitamin A, vitamin K, and the taxanes. The taxanes (diterpenes), such as pakilitaxel, are used for treating cancer (Heinig and Jennewein (2009) African J. Biotech. 8:1370-1385), Terpenes in cannabis have been described. See, Flores-Sanchez and Verpoorte (2008) Phytochem. Rev. 7:615-639, and US2015/0080265 Elzinga and Raber and US2015/0152018 of Raber and Elzinga, each of which is incorporated herein in its entirety.

The present disclosure provides extracts, oils, slurries, suspensions, cooled viscous compositions, warmed viscous compositions, pure compositions, compositions comprising purified compounds, compositions consisting of purified compounds optionally with one or more solvents, and combinations of pure compounds, of the following: Hemiterpenes: Examples of hemiterpenes that do not necessarily have an odor, are 2-methyl-1,3-butadiene hemialboside, and hymenoside; Monaterpenes: pinene; alpha-pinene, beta-pinene, cis-pinane, trans-pinane cis-pinanol, trans-pinanol (Erman and Kane (2008) Chem. Biodivers. 5:910-919) limonene; linalool; myreene; encalyptol; alpha-phellandrone; beta-phellandrene; alpha-ocimene; beta-ocimene, ocimene, delta-3-carene; fenchol; sabinene, borneol, isobotneol, camphene, camphor, phellandrene, alpha-phellandrene, alpha-terpinene, geraniol, linalool, nerol, menthol, myrcene, terpinolene, alpha-terpinolene, beta-terpinolene, gamma-terpinolene, delta-terpinolene, alpha-terpincol, trans-2-pinanol, Sesquiterpenes: caryophyllene; beta-caryophyllene, caryophyllene oxide, humulene, alpha-humulene, alpha-bisabolene; beta-bisabolene; santalol; selinene; nerolidol, bisabolol; alpha-cedrene, beta-cedrene, beta-eudesmol, cudesm-7(11)-en-4-ol, selina-3,7(11)-diene, guaiol, valencene, alpha-guaiene, beta-guaiene, delta-guaiene, guaiene, farnesene, alpha-farnesene, beta-farnesene, elemene, alpha-elemene, beta-elemene, gamma-elemene, delta-elemene, germacrene, germacrene, germacrene B, germacrene C, germacrene D, germacrene E, Diterpenes: oridonin, Triterpenes: ursolic acid; oleanolic acid; [0012]"1.5 ene": guaia-1(10),11-dienecan be characterized as a 1.5 ene", Guaia-1(10),11-diene is halfway between a monoterpene and diterpene, in terms of how many isoprenoid units are present. Monoterpene is C10H16, and diterpene is C20H32. Guaia-1(10),11-diene is C1sH24. Isoprene is CsHs (two double bonds).

The present disclosure provides compounds in hops (Humulus lupulus). These compounds include myrcene, alpha-humulene, and beta-caryophyllene, which are in hop essential oils. Other hop compounds are bitter acids, such as alpha-acid and beta-acid (humulone and lupulone), which are prenylated polyketide derivatives. Prenylated flavonoids are also in hops, and these include xanthohumol, desmethylxanthohumol, isoxanthohumol, 8-prenylnaringenin, and 6-prenylnalingenin (Wang et al (2008) Plant Physiol. 148: 1254-1266; Nagel et al (2008) Plant Cell, 20:186-200).

Extracting Compounds

Extracting compounds from natural products can use methods and reagents, for example, as described by US2015/0152018 of Raber and Elzinga, which is incorporated herein by reference. Extractions can use a single step, or multiple sequential steps, and can use water, acetone, alcohol, butane, vegetable oil, mixtures thereof, and the like. Extraction methods can use chopping, shredding, homogenization, sonication, vortexing (e.g., vibrating a test tube using a vibrating rubber cup to produce a vortex), centrifugation, phase separation, filtering (e.g., paper filter, sintered glass filter, Millipore® filter), incubating, heating, rotary evaporation, distillation any combination thereof, and so on. Analytical scale methods of the present disclosure include acetone, methanol, ethanol, chloroform/methanol, chloroform/ethanol, and so on. The sample can be from any plant or other natural product, including Cannabis sativa, Humulus lupulus, or other plant strains.

Equipment

Dual asymmetrical centrifuge (DAC) differs from conventional centrifugation by an additional rotation of the sample around its own vertical axis. While the conventional centrifugation constantly pushes the sample material outwards, this additional rotation constantly forces the sample material towards the center of the centrifuge. This combination of two contra rotating movements results in shear forces and thus, in efficient homogenization (Massing et al (2008) Dual asymmetric centrifuigation (DAC)—a new technique for liposome preparation. J. Control Release. 125:16-24). Non-limiting information about one model of DAC reveals that, the dual asymmetric DAC 150 FV-K works by spinning a high speed-mixing arm at speeds up to 3700 rpm in one direction while the basket rotates in the opposite direction, thus, the name—dual asymmetric centrifuge. This combination of forces in different planes enables fast mixing, and yet the precision construction of each machine gives it a balance that allows quiet operation (Synergy Devices (Oct. 11, 2006) Benefits of non-invasive dual asymmetric mixing). Non-limiting information on another model of DAC reveal that the mixing procedure is based on the double rotation of the mixing cup (hence the designation dual asymmetric centrifuge). This combination of centrifugal forces acting on different levels enables very rapid mixing of the entire cup. The precision construction of the units gives the opposing forces an equilibrium with near zero vibration and low-noise operation.

Cannabinoids and powders are preferably mixed with DAC mixer, and can also be mixed with, for example, ribbon blender, kitchen blender, V-type blender, double cone blender, fluidized bed mixer, mass mixer, and so on.

Ribbon Blenders consist of a U-shaped horizontal trough and a ribbon agitator. A ribbon agitator consists of inner and outer helical agitators. The outer ribbon moves materials in one direction and the inner ribbon moves materials in the opposite direction. The ribbons rotate at about 300 fpm moves materials both radially and laterally (Charles Ross and Co. Hauppauge, N.Y.).

V-type blenders consist of two cylinders arranged in a "V" shape with an angle of 80°. A manually actuated inspection and loading port is at the end of each cylinder. The product outlet is located where the two cylinders are joined and is fitted with a butterfly valve. The geared motor and the bearing system are in the lateral supports holding the blender body. Solids are introduced into the blender through an aperture. Mixing performance is of 50%, that is, with each turn of the blender, the product located in the two cylinders moves into the central common section and this is repeated continuously (Inoxpa, Santa Rosa, Calif.).

Double cone blenders are described. The blender has two cone-shaped sections welded at their bases to a central cylindrical section. Axis of rotation is perpendicular to the cone axis and passes through the cylindrical section. A motor is located at one of the two lateral supports holding the blender body. Solids are introduced via an aperture. Mixing takes place axially as a result of the powder moving through the different sections. The mixture is discharged through a hermetically closing butterfly valve (Inoxpa. Santa Rosa, Calif.).

Fluidized bed mixers resemble a ribbon, paddle or plow blenders, but with differences. Instead of a single shaft turning agitator blades slowly within a U-shaped trough, the fluidized bed mixers may have two counter-rotating shafts turning paddle agitators rapidly within two, parallel U-shaped troughs. Flat, angular paddles with overlapping paths sweep material from the troughs toward the center and upward, causing the material to become airborne in a fluidized zone above the longitudinal centerline of the mixing chamber where particles intersperse. Fluidized zone is a suitable location for spraying high- or low-viscosity liquids, which disperse more readily throughout the batch than in ribbon, paddle and plow blenders. Consequently, liquids can be added in higher volumes while maintaining free-flowing characteristics of the batch. Fluidized mixing action creates less shear than with other agitated blenders (Munson Machinery, Utica, N.Y.).

DAC mixers are available from, e.g., Synergy Devices, Ltd., High Wycombe, Bucks, United Kingdom; FlackTek, Inc., Landrum, S.C. Ribbon blenders are available, e.g., from Charles Ross and Co., Hauppauge, N.Y. Kitchen blenders are available from, e.g., Vitamix, Cleveland, Ohio; Sunbeam Products, Inc. (Mixmaster®). V-type blenders are available from, e.g., Inoxpa, Santa Rosa, Calif.; and Charles Ross and Co., Hauppauge, N.Y. Double cone blenders are available from, e.g., Kemutec Group, Inc. Bristol, Pa. Fluidized bed mixers are available from, e.g., Munson Machinery, Utica, N.Y.

Viscometers and rheometers are available (Brookfield Ametek, Middlefield, Mass. 02346). Instructions for using viscometers and rheometers are available (Brookfield DV3T Viscometer Operating Instructions, Manual No. M13-2100-A04145 (126 pages); Brookfield RS-CPS+Rheometer Operating Instructions Manual No. M0S-218-B0212 (62 pages); Brookfield Model BF35 Viscometer Installation, Operation and Maintenance Instructions Manual No. M13-10000 (23 pages). Rotational rheometers (Kinexus ultra+, Kinexus pro+) and capillary rheometers (Rosand RH200) are available from Malven Instruments, Malvern, United Kingdom.

Both viscometer and rheometer can measure viscosity vs. shear rate and viscosity vs. temperature. Rheometers operate in both controlled stress as well as controlled rate modes of operation. Rheometers provide a more general capability for theological evaluation of flow behavior compared to viscometers. Controlled stress tests are specifically applicable to the direct measurement of yield stress and creep. Yield stress characterizes the force needed to initiate flow of an ointment; squeezing product out of a tube is a specific example. Creep testing measures the flow behavior under a constant force like gravity, e.g., a lotion's ability to hold position after application and not drip or run is the type of situation that you evaluate with this test (see, e.g., McGregor, *RG Viscomeier vs. Rhemneter: Which is the Better Choice?* Brookfield Ametee, Middlefield, Mass. (2 pages)). Most viscometers operate by rotating a spindle in the sample. Viscosity is determined by measuring resistance to this rotational force. Viscometers are simpler machines than rheometers. Spindle movement in a viscometer is in one direction, which allows the measurement of viscosity. Rheometers can apply oscillatory and rapid step changes in stress and strain, and can therefore determine viscoelastic properties (providing information on the structural properties of the sample) as well as flow properties (see, e.g., Carrington and Langridge (August 2005) Laboratory News. Malvern Instruments (2 pages)).

The mixers, rheometers, viscometers, manuals, and the like, that are disclosed herein do not imply any limitation on the present disclosure.

Analysis; Chromatography

An analysis step may comprise separating substances from a mixture, genetic analysis, chemotaxonomic analysis, compound extraction, gas chromatography flame ionization detection, chemical formula identification, chromatography, or any other analytical chemistry technique described herein or otherwise known in the art.

Terpenes can be identified based on their chromatography profiles or other chemical properties of the analyzed compounds. Terpenes may be quantified based on their mass fraction percent weight, mole fraction, percentage by volume, or the like. The compositions and their quantities can be assembled as a library or database, or any other data management format known in the art. In embodiments that involve creating a prepared blend that mimics a naturally-occurring composition the synthetic blend may comprise all naturally-occurring terpenes, all synthetic terpenes, or a combination thereof.

Terpenes that can be analyzed include alpha-bisabolol, beta-caryophyllene alpha-humulene, linalol myrcene, alpha-pinene, beta-pinene, and terpinolene.

Terpenes can be purified, analyzed, and identified, by various techniques, including high pressure liquid chromography (HPLC), gas chromatography, and other, chromatographic techniques (see, e.g., Musenga et al (2006) J. Sep. Sci. 29:1251-1258; Yang et al (2009) J. Nat. Prod. 72:484-487; Jella et al (1998) J. Agric. Food Chem. 46:242-247; Andrea et al (2003), J. Agric. Food Chem. 51:4978-4983; Villa et al (2007) J. Phann. Biomed. Anal. 44:755-762).

Terpenes and other chemicals can be analyzed by mass spectrometry (Hendriks and Bruins (1983) Biol. Mass Spectrom. 10:377-381; gas chromatography-mass spectrometry (GC-MS) (Gadulo et al (2010) J. Food Sci. 75:C199-207), nuclear magnetic resonance (NMR) (Mucci et al (2013) Food Chem. 141:3167-3176; Mang et al (2013) Food Chem. 138:208-213), mass spectroscopy, and Matrix-Assisted Laser Desorption/Ionization Time-of-Flight mass spectrometry (MALDI-TOS) (Scalarone et al (2005) J. Mass Spectrom. 40:1527-1535).

Terpene analysis can be performed on a Shimadzu GC-2010 GC/FID with helium as the carrier gas. Colunms of use include, Phenomenex ZB-5MS GC column. Additional columns that can be used: Agilent HP-5MS, Agilent DB-5, and Supelco SPB-5, Standard terpenes are available from Sigma-Aldrich (St. Louis, Mo.). Samples and standards can be prepared in ethyl acetate (EtOAc). Cannabinoids, terpenes, and other compounds can be separated with GC colums, for example ZB-35 column with a film that has 65% monomers that are —Si(methyh)-O— and 35% monomers that are —Si(benzyh)-O—. ZB-1701 with a film with 86% monomers that are —Si(methyh)-O— and 14% monomers that are —Si(benzyl, methyb-cyano)-O—.

Fluids, Slurries, Gels, Solvents

In embodiments, the present disclosure provides a formulation that comprises a fluid that is a transparent liquid, a translucent liquid, an opaque liquid, a slurry, an emulsion, a suspension, a gel, and the like. In other embodiments, the present disclosure provides a formulation that consists of a fluid that is a transparent liquid, a translucent liquid, an opaque liquid, a slurry, an emulsion, a suspension, a gel, and the like. The designation of liquid, slurry, emulsion, gel, and so on, refers to this characterization as determined at room temperature (about 23 degrees centigrade).

The present disclosure encompasses compositions and methods that comprise solvents, such as triacetin, dipropylene glycol, diethyl phthalate, isoparaffins, paraffins, silicon oils, perfluorinated aliphatic ethers, glycol ethers, glycol ether esters, esters, or ketones, propylene glycol, ethanol, triacetin, phytol, water, dimethicone or cyclomothicone, and so on. Solvents such as propylene glycol are commonly used in electronic cigarette (e-cigarette) formulations. The addition of 10-70% cannabinoids to a mixture of terpenes and propylene glycol creates an emulsified mixture ideal for use in e-cigarettes.

Reagent-grade chemicals, such as sugar alcohols (sucrose, mannitol, inositol, xylitol, sorbitol, maltitol), fluorettes, sweeteners, pigments, emulsifiers (saponin, lecithin, Tween 80), detergents, salts (NaCl, KCl, Na2CO3. CaHPQ4, MgCQ3 fatty acids (stearic acid, magnesium stearate, sodium stearoyl lactylate), proteins (gelatin, zein, whey), amino acids including branched-chain amino acids, carbohydrates (microcrystalline cellulose, pectin, maltodextrin, sodium alginate, alginic acid, xanthan gum, cyclodextrins), and polymers (hydroxypropyl cellulose, carboxymethyl cellulose, polyvinylpyrrolidone (PVP)) are available (Sigma-Aldrich, St, Louis, Mo.; Fisher Scientific, Pittsburgh, Pa.). Hydrocolloids, such as alginate, biopolymers (xznthan gum and scleroglucan), carrageenan, galactomannan (locust bean gum) and pectin are available (Cargill, Inc., Minneapolis, Minn.). Home use products such as granulated sucrose, powdered sucrose, flour, starch such as corn starch, talc, gelatin, and sweeteners (aspartame, saccharin, stevia, sucralose) are available (Safeway, Inc., Pleasanton Calif.; Vons, Arcadia, Calif.; Raley's, West Sacramento, Calif.).

The recited reagents, suppliers, manufacturers, vendors, and the like, do not imply any limitation on the present disclosure.

SUMMARY OF THE DISCLOSURE

Briefly stated, the present disclosure provides method for preparing a composition that comprises a plurality of coated particles, the method comprising the steps of: (i) Placing a plurality of edible particles in a container, wherein the container comprises a bottom and a retaining wall or sides, wherein the plurality of edible particles in the container is capable of receiving and supporting an added cannabinoid extract or resin and the plurality of edible particles is capable of substantially preventing contact of the cannabinoid extract or resin with the bottom of the container and is also capable of substantially preventing contact of the cannabinoid extract or resin with the retaining wall or sides, (ii) Placing a cannabinoid extract or resin on top of the plurality of edible particles, wherein the cannabinoid extract or resin does not substantially contact the bottom of the container, and does not substantially contact the retaining wall or sides of the container, and (iii) Mixing until the cannabinoid extract or resin coats the edible particles to produce a coating, resulting in a composition of homogeneously coated edible particles, and wherein the homogeneously coated edible particles possess a homogeneity.

Also provided is the above method, further comprising the step of initiating device-mediated mixing of the cannabinoid extract or resin with the plurality of edible particles using a mixer, wherein the mixing generates a mixture. Also embraced is the above method, wherein at the step where the cannabinoid extract or resin is placed on top of the plurality of edible particles, less than 10% of the extract or resin at this step contacts the bottom of the container, retaining wall, or sides. Further contemplated is the above method, wherein the homogeneously coated particles have a homogeneity, and where the homogeneity is definable by the range of values for specific surface area, in a given sample of at least 1000 coated particles. Additionally provided is the above method, wherein the homogeneously coated particles have a homogeneity, and where the homogeneity is definable by the range of values for [[mass coating]/[mass of coated particle]], in a given sample of at least 1000 coated particles.

In yet another embodiment, what is provided is the above method, wherein the container is an integral part of a mixer. Also embraced, is the above method, wherein the container is not an integral part of a mixer. Further contemplated is the above method, wherein the container has one or more internal sides and wherein the one or more internal sides of the container comprises discrete retaining walls, discrete sides, or a tubular retaining wall. In another aspect, what is provided is the above method, wherein the device-mediated mixing is with a dual asymmetrical centrifuge (DAC) mixer; or wherein the device-mediated mixing is with a DAC mixer, ribbon blender, kitchen blender, V-type blender, double cone blender, fluidized bed mixer, or mass mixer, or with any combination thereof; or wherein the device-mediated mixing is not with a mixer other than a DAC mixer.

Moreover, the present disclosure provides the above method, wherein the coating comprises at least one cannabinoid. Also provide is the above method, wherein the coating comprises at least one cannabinoid, and where the product is configured for eating as is, or is configured for combining with a food prior to cooking followed by cooking the combination of the product and the food.

Additionally, what is embraced is the above method, wherein the plurality of coated particles comprises coated sugar particles, coated flour particles, or coated salt particles, or any combination thereof. Moreover, what is contemplated is the above method, further comprising coating the particle with one or more of a secondary coating substance, wherein the secondary coating substance is an emulsifier, pigment, or odorant, wherein coating the particle with the secondary coating substance can be prior to, after, or simultaneously with coating the particle with the primary coating substance.

Moreover the disclosure provides the above method that produces an edible product that is capable of use as an ingredient for the preparation of a cooked food; or that produces a dry instant powder for use in adding to or mixing with water and making a flavored drink; or that produces a dry instant powder for use in adding to or mixing with water and making a medicated drink; or wherein the edible particles comprises one or more of a sugar, a non-sugar sweetener, a salt, or a protein.

In another aspect, the disclosure provides the above method, further comprising adding one or more of an emulsifier, a pigment, a flavoring compound, or a pharmaceutical, to the plurality of edible particles. Also provided is the above method, further comprising adding one or more of an emulsifier, a pigment, a flavoring compound, or a pharmaceutical, to the plurality of edible particles prior to initiating mixing. Furthermore, what is embraced is the above method, further comprising adding one or more of an emulsifier, a pigment, a flavoring compound, a pharmaceutical, to the plurality of edible particles during the mixing. Additionally, the disclosure provides the above method, further comprising the step of manual mixing prior to initiating device-mediated mixing.

In an embodiment with reduced explosion risk, the disclosure provides the above method, where the method is characterized by reduced explosion risk from explosions originating from dust, wherein the reduced explosion risk is provided by one or more of: (a) Limiting the plurality of edible particles to a mass of 100 grams or less; (b) Providing a ventilator that removes dust by way of ventilation; (c) Limiting or not using any compounds that generate hydroxymethylfurfural; (d) Limiting or eliminating flammable solvents; and (e) Limiting or eliminating use of elevated temperatures that can ignite a flammable solvent.

In embodiments with defined ratios, the disclosure provides the above method, wherein the plurality of edible particles consists of powdered sugar, wherein the homogeneously coated edible particles has a coated particle mass (grams), and wherein the plurality of edible particles has a mass of 87% the coated particle mass and the cannabinoid extract or resin has a mass of 13% the coated particle mass.

In a composition embodiment, what is provided is a composition of coated particles produced by the above method. In an insufflatable powder embodiment, what is provided is an insufflatable powder comprising a composition of coated particles produced by the above method. Also provided is a confection or candy that comprises a composition of coated particles produced by the above method; as well a dry premix for making a beverage, wherein the dry premix comprises a composition of coated particles produced by the above method.

In a paste embodiment, the disclosure embraces a method for preparing a composition that comprises a plurality of coated particles, the method comprising the steps of: (i) Placing a plurality of edible particles in a container, wherein the container comprises a bottom and a retaining wall or sides, wherein the plurality of edible particles in the container is capable of receiving and supporting an added cannabinoid extract or resin and the plurality of edible particles is capable of substantially preventing contact of the cannabinoid extract or resin with the bottom of the container and is also capable of substantially preventing contact of the cannabinoid extract or resin with the retaining wall or sides, (ii) Placing a composition comprising a cannabinoid extract or resin on top of the plurality of edible particles, wherein the cannabinoid extract or resin does not substantially contact the bottom of the container, and does not substantially contact the retaining wall or sides of the container, and (iii) Mixing until the cannabinoid extract or resin coats the edible particles to produce a coating, resulting in a composition of homogeneously coated edible particles, and wherein the homogeneously coated edible particles possess a homogeneity. What is further provided is the above paste embodiment method, wherein the composition comprising a cannabinoid extract resin further comprises emulsifier, and wherein the composition is a paste. Moreover, what is provided is the above paste embodiment method, wherein the composition comprising a cannabinoid extract or resin further comprises saponin emulsifier, and wherein the composition is a paste. Also provided are compositions made using paste embodiment method.

Methods of the Present Disclosure

Processes of the present disclosure create an intermediate product used in cooking (edible production) or, alternatively, an instant powder to create a medicated flavored drink when added to water. The end product of the process can be sugar, flour, salt or any other ingredient used in the preparation of an edible product, but coated with a very standardized amount of cannabinoids. Optionally, the process can add emulsifiers, pigments, odorants or other functional ingredients to the mix. One final product is a powder coated with a standardized amount of cannabinoids for manufacturers of edibles or home cooks to use. Cannabinoid concentrates are difficult to handle, existing as a viscous, sticky semi-solid at room temperature. By precoating it on the main ingredient of an edible, the difficulty of handling the material is greatly reduced and the cook does not have to worry about homogenous distribution in the end product. Another end product is a dry drink mix prepared by coating the cannabinoids onto sugar or other sweetener in combination with an emulsifier and optional pigment and flavor. This powder could be added to water to create a medicated drink. The emulsifier may be critical in this application as cannabinoids and water don't usually mix.

Compositions of the Present Disclosure

Compositions can be defined in terms of one or more of the following parameters:
(1) Identities of cannabinoids in the starting material, that is, an extract; (2) The cannabinoids of a coated powder; (3) The chemical composition of the powder or the particles to be used in the coating process (4) The range of diameters of particles on the powder prior to coating; (5) The range of diameters of the coated powder; (6) The amount of loading that was obtained. For example, a loading of 15% can mean that 15 of cannabis extract can be coated onto 85 g powder to yield 100 grams of product in the end. An edible particle can "support" a coating, where "supporting" encompasses for example one of more of mediating adhesion, absorbance (draw inside to some extent), adsorbance (stick to outside).

The above list of parameters does not imply limitation on the present disclosure. Compositions of the present disclosure can be further defined by statistical parameters that related to, for example, homogeneity. In a preferred embodiment the present disclosure provides a composition comprising coated particles, where the particles are coated with at least one type of cannabinoid, and where the homogeneity of the coating has a standard deviation (SD) of below 0.05 (mg cannabinoid/gram coated particles), and where the cannabinoid THC.

In alternative embodiments, the disclosure provides coated particles, or e powders, with homogeneity of a coating with SD under 1.0, under 0.7, under 0.6, under 0.5, under 0.4, under 0.3, under 0.2, under 0.1, under 0.09, under 0.08, under 0.07, under 0.06, under 0.05, under 0.04, under 0.03, under 0.02, under 0.01, and the like. These standard deviations can be applied to the degree of spread of amount of coating per particle, that is, the SDs can be applied to describe a given batch of coated particles.

Where many apples of coated particles are taken from a large batch of coated particles, the homogeneity of coating (from sample to sample) will be a function of the homogeneity of this coating and also a function of the reproducibility of the machine. Here, it useful to test reproducibility of the machine by conducting repeated measurements on the exact same sample.

Alternatively, these standard deviations can be applied to a standard composition of coated particles, where the standard deviations are instead use characterize reproducibility of the measurement of coating homogeneity. The reproducibility of any given machine that is used for manufacturing foods or pharmaceuticals is determined by validation. For example, validation of a machine can be determined by an Installation Qualification Operational Qualification (IQ/OQ) (See, e.g., Bansal et al (2004) *Qualification of Analytical Instruments for Use in the Pharmaceutical Industry: A Scientific Approach*. AAPS PharmSciTech. 5:151-158).

Ratio of [Mass of Non-Coated Particles]/[Mass of Cannabinoids] Used to Create Coated Particles For every 100 grams of coated particles, the ratio of [particle mass] to [cannabinoid extract or resin mass], can be 87/13, 88/12, 89/11, 90/10, 91/9, 92/8, 93/7, 94/6, 95/5, 96/4, 97/3, 98/2, or 99/1. Also, for every 100 grams of coated particles, the ratio of particle mass to cannabinoid extract or resin mass, can be 86/14, 85/15, 84/16, 83/17, 82/18, 81/19, 80/20, 79/21, 78/22, 77/23, 76/24, 75/25, and so on. What is also encompassed are ranges of particle masses and cannabinoid masses that are used to make the equivalent of 100 grams of coated particles. For example what can be encompassed is the range of 85/15 to 90/10.

Influence of Heat on Coating Powders with Cannabinoids

Cannabinoids (cannabis extract, pure cannabinoids, high THC extract, high CBD extract or combination thereof) are a viscous semi-solid at room temperature but a free flowing liquid above approximately 50 degrees C. Regarding temperature, it is likely that during the mixing the heat generated by the friction during mixing causes the otherwise solid cannabinoids to liquefy and homogenously coat the solid non-cannabinoid matrix. In the process there are the following steps: (1) Powder is added to a container. (2) Cannabinoids are added on top of the powder so they do not stick to the side of the container. (3) The mixer is turned on causing the powder and cannabinoid lump to move, the moving creates a lot of friction, the friction sloughs cannabinoids from the lump onto the powder until the lump disappears and the cannabinoids are completely dispersed onto the powder. The viscous cannabinoids get coated onto the powder by the mixer. An optional methods step is manual premixing of the cannabinoids sitting on top of the powder, before turning on the electric mixer.

In embodiments, the present disclosure provides a method comprising the step of adding powder to a container, wherein the powder comprises powder particles, adding cannabinoids to the top of the powder to create a lump or lumps of cannabinoids on the powder, mixing with an electric mixer to create a mixture, where friction during mixing causes the temperature of the mixture to increase, wherein the increased temperature enhances sloughing off of cannabinoids from the lump or lumps and consequent dispersal as a coating on the powder particles, wherein mixing is continued until at least 60%, at least 90%, at least 95%, at least 98%, or at last 99.5% of the cannabinoids are coating the powder particles.

Also provided is the above method, where the cannabinoids are added to the top of the powder with manual mixing and where less than 10% less than 5%, less than 2%, or less than 0.5% of the cannabinoids adhere directly to the side of the container prior to mixing, with an electric mixer, or where, the cannabinoids are added to the top of the powder without manual, mixing, and where less than 10%, less than 5%, less than 2%, or less than 0.5% of the cannabinoids adhere directly to the side of the container prior to mixing with an electric mixer.

Temperatures of powders can be obtained in real-time during mixing, for example, by a temperature probe that is inside the mixture during the mixing process. Temperature probes are available from, e.g., Philips Medical Systems, The Netherlands. In one embodiment, heating is accomplished only by friction during mixing, and this embodiment can exclude external sources of heat, can exclude external cooling sources, or can exclude external sources of heat and cooling. Alternatively, the present disclosure can provide external sources of heat, external sources of cooling, or both external sources of heating and cooling.

Contact of Resin or Extract with Container

The methods of the present disclosure optionally minimize contact of the resin or extract with the bottom and sides of mixing container, at the step with resin or extract is placed on top of an in contact with coated powder. In various embodiments, a cannabinoid extract or resin is placed on top of the plurality of edible particles, not substantially contact the bottom and the retaining wall or sides, where the term "not substantially" means that less than 50% of the resin or extract is in contact, less than 40% of the resin or extract is in contact, less than 30% of the resin or extract is in contact, less than 20% of the resin or extract is in contact, less than 10% of the resin or extract is in contact, less than 5% of the resin or extract is in contact, less than 2% of the resin or extract is in contact, less than 1% of the resin or extract is in contact, less than 0.1% of the resin is in contact, and so on. The present disclosure encompasses use of a mixture of resin plus extract, for example, where this mixture is placed on top of an in contact with a coated powder.

Contact of Resin or Extract with Bottom or Sides of Container

When resin or extract is placed on top of a plurality of edible particles, it is possible that a small proportion of the resin or extract can contact the bottom or sides of the container, even in absence of concurrent mixing. Contact may occur where the resin or extract is not substantially centered on top of the particles and where it is placed in a lopsided manner that allows some contact with the sides. Contact with the bottom or sides may occur if too much force is used in delivering the extract or resin to the top of the particles.

Cooling

A preferred temperature of the cooled container, powder, and cannabinoids is minus 20 degrees C. A preferred temperature range degrees to 20 degrees. Other contemplated temperature ranges are e.g., −5 degrees to +5 degrees; −10 degrees to 10 degrees; −15 degrees to +15 degrees; −25 degrees to +25 degrees; −30 degrees to +30 degrees; −40 degrees to +40 degrees; and −78 degrees and +78 degrees. Minus 40 degrees C. is a preferred process temperature, because it is often the lower limit of some recirculators used in industrial processes. Further temperature ranges are, e.g., −20 degrees to +5 degrees; −20 degrees to +10 degrees; −20 degrees to +15 degrees; −20 degrees to +5 degrees; and −20 degrees to +30 degrees. Additional temperature ranges are, e.g., −5 degrees to +20 degrees; −10 degrees to +20 degrees; −15 degrees to +20 degrees; −25 degrees to +20 degrees; −30 degrees to +20 degrees −40 degrees to +20 degrees and −78 degrees to +20 degrees, Liquid nitrogen (minus 196° C.) is the lowest practical temperature that could potentially ever be used.

In some embodiments, there is no active cooling during the mixing process, and here, cooling relics only on precooling the mixture, precooling the container and mixer, or precooling the mixture, the mixer, and the container. In other embodiments, there is active cooling during the mixing process. Active cooling can be achieved by using dry ice in chamber, e.g., by adding dry ice to the poweder and directly in contact with the powder prior to mixing, by adding dry ice to the powder composition and directly in contact with the poweder during mixing, or alternatively by pre-cooling mixing chamber, or by a refrigerator that uses electricity and a coolant. The present disclosure can exclude methods, instrumentation, and compositions that are made, that employ active cooling.

Measuring Coating Uniformity

Coated particles can be assessed for coating uniformity and other physical properties by techniques such as light microscopy, electron microscopy, and confocal raman microscopy. See, Schoenherr et al (2009) European J. Pharmaceutical Sciences, 38:47-54; Bandari et al (eds.). (2013) Handbook of Food Particles: Processes and Properties. Woodhead Publ. Ltd. (page 347); Goff et al (1987) Food Microstructure. 6:193-198; Ishizaka et al (2008) Chem. Phann. Bull. 56; 1398-1394; Werner S R (2005) Air-Suspension Coating of Dairy Powders: A Micro-Level Process Approach. Thesis. Massey University, New Zealand; and U.S. Pat. No. 5,158,804 of Alkan et al, which is incorporated by reference herein in its entirety.

Influence of Heat on Evaporation, Oxidation, and Viscosity

The maximally permitted temperature range, during processing with, for example, a DAC mixer, is about 180 degrees C. At above 180 degrees C., what is expected are the adverse consequences of severe evaporation and oxidation of cannabinoids.

This is about heat generated by an DAC mixer and the consequent reduction in viscosity. Cannabis extracts that will be coated on the powders generally start at $1\times10^6$ centipoise (cP) at room temperature. These are in the $1\times10^8$-$1\times10^9$ centipoise (eP) range when frozen. The sloughing of cannabinoids is likely the most efficient in the $1\times10^4$-$1\times10^5$ centipoise (eP) range. In some embodiments, the lowest acceptable viscosity (as it occurs in the mixer during the mixing process) may be $1\times10^4$ centipoise (cP). In other embodiments, the lowest acceptable viscosity is $30\times10^4$ cP (more viscous), $20\times10^4$ cP, $10\times10^4$ cP, $5\times10^4$ eP, $2\times10^4$ cP, $1\times10^4$ eP, $0.5\times10^4$ cP, $0.2\times10^4$ cP, $0.1\times10^4$ cP, $0.05\times10^4$ cP, $0.02\times10^4$ cP, $0.01\times10^4$ cP (less viscous), and the like.

In exclusionary embodiments, the present disclosure can exclude any process, method, and composition made by said process or method, where the composition being mixed or sloughed never reaches a lowest acceptable viscosity of, for example, $30 \times 10^4$ cP (more viscous), $20 \times 10^4$ cP, $10 \times 10^4$ cP, $5 \times 10^4$ cP, $2 \times 10^4$ cP, $1 \times 10^4$ cP, $0.5 \times 10^4$ cP, $0.2 \times 10^4$ cP, $0.1 \times 10^4$ cP, $0.05 \times 10^4$ cP, $0.02 \times 10^4$ cP, $0.01 \times 10^4$ cP less viscous), and the like.

In other exclusionary embodiments, the present disclosure can exclude any process, method, and composition made by said process or method, where the composition being mixed or sloughed never reaches a temperature that is correlated with a given lowest acceptable viscosity. For making standard curves that correlate temperature with viscosity, one can use a temperature-controlled rheometer (e.g., from ThermoFisher Scientific (Waltham, Mass.) or Anton Paar USA (Ashland, Va.)).

Powder Mesh Sizes

The disclosure provides powders with powder mesh sizes in a range of, for example, 1-100 um, 1-200 um, 1-400 um, 1-800 um 1-1000 um, 1-2000 um, 1-3000 um, 1-4000 um, and 1-5000 um. Also provided is powder with size in range of, 10-100 um, 10-200 um, 10-400 um, 10-800 um, 10-1000 um, 10-2000 um, 10-3000 um, 10-4000 um, and 10-5000 um. Also provided is powder with size in range of, 20-100 um, 20-200 um, 20-400 um, 20-800 um, 20-1000 um, 20-2000 um, 20-3000 um, 20-4000 um, and 20-5000 um. Also provided is powder with size in range of, 40-100 um, 40-200 um, 40-400 um, 40-800 um, 40-1000 um, 40-2000 um, 40-3000 um, 40-4000 um, and 40-5000 um. Also provided is powder with size in range of, 60-100 um, 60-200 um, 60-400 um, 60-800 um, 60-1000 um, 60-2000 um, 60-3000 um, 60-4000 um, and 60-5000 um. Also provided is powder with size in range of, 80-100 um, 80-200 um, 80-400 um, 20-800 um, 80-1000 um, 80-2000 um, 80-3000 um, 80-4000 um, and 80-5000 um. Also provided is powder with size in range of, 100-200 um, 100-400 um, 100-800 um, 100-1000 um, 100-2000 um, 20-3000 um, 100-4000 um, and 100-5000 um. Also provided is powder with size in range of, 100-100 um, 100-200 um, 100-4000 um, 100-800 um, 1.00-1000 um, 100-2000 um, 20-3000 um, 100-4000 um, and 100-5000 um. In powder mesh size ranges with a low upper limit, what is provided is a range of, 1-90 um, 1-80 um, 1-70 um, 1-60 um, 1-50 um, 1-40 um, 1-30 um, 1-20 um, and 1-10 um. Also provided are powders with mesh sizes in the ranges, 5-100 um, 5-90 um 5-80 um, 5-70 um, 5-60 um, 5-50 um, 5-40 um, 5-30 um, 5-20 um, and 5-10 um, and the like. Also provided are powders with mesh size in the range of, 10-100 um, 10-90 um, 10-80 um, 10-70 um, 10-60 um, 10-50 um, 1.0-40 um, 10-30 um, and 10-20 um. Also provided are powders with mesh size in the range of, 20-100 um, 20-90 um, 20-80 um, 20-70 um, 20-60 um, 20-50 um, 20-40 um, 20-30 um. A preferred range of powder mesh size is 1-100 um.

Powder Mesh Size Exclusionary Embodiments

In exclusionary embodiments, the present disclosure can exclude any powder that has a mesh size that is essentially the same as one of the above ranges (or that fits into and is smaller than one of the above ranges). Also, in exclusionary embodiments, the present disclosure can exclude any composition that was made with a powder having a mesh size that is essentially the same as, one of the above ranges (or that fits into and is smaller than one of the above ranges). Also, in exclusionary embodiments, the present disclosure can exclude any method that involves a powder having a mesh size that is essentially the same as one of the above ranges (or that its into and is smaller than one of the above ranges).

Emulsifier Embodiments

Formulas disclosed herein can optionally include one or more emulsifiers. An emulsifier can enhance absorption of cannabinoids by the human body, and can produce stronger effects than a solution without them. These effects can be physiological, medicinal, sensory (taste, smell, palatability), aesthetic, psychological, and any combination thereof. Also, emulsifier can enhance homogeneity of one or more or all embodiments of the product Emulsifiers include, e.g., Tween 20®, Tween 65®, Tween 80®, Macrogol (25)-cetostearyl ether Polyethylene glycol 1100 mono(hexadecyl/octadecyl) ether; Lutrol® P68 Poloxamer 188 Poly(ethylene glycol)-block-poly(propylene glycol)-block-poly(ethylene glycol); saponin; Creemophor ELP PEG-35 castor oil Polyoxyl 35 Hydrogenated Castor oil Polyoxyl-35 castor coil Lutrol® E300 Macrogol 300 PEG Poly(ethylene glycol) Polyethylene glycol 300; Lutrol® E 400 Macrogol 400 PEG Poly (ethylene glycol) Polyethylene glycol 400, and the like (Sigma-Aldrich, St. Louis, Mo.). Descriptions of emulsifiers for enhancing absorption are described for the indicated emulsifiers, e.g., polyglycerol (Wilson (1998) Food Chem. Tox. 36:711-718), sucrose fatty acid ester (Weangsrupanaval et al (2005) J. Nutr. 135:1738-1744), and Tween 80 (Krondl et al (1964) Gut. 5:607-610).

Compositions with a Plurality of Powder Types

Embodiments with two or more types of powders are provided. For example, methods and compositions involve a first step, making a highly concentrated powder which consists of cannabinoids that coat powdered sugar, and that involves a second step of using a powder blender to blend down to lower concentrations, where this blending down to lower concentrations uses a different type of powder, such as citric acid. One embodiment is a sour candy confection, that comprises a method, and confections produced by the method. The method comprises making a concentrated 10% powdered sugar and then blending that down into a mixture of citric, tartaric, granular sugar, emulsifier, and optionally with one or more pigments.

Determining Homogencity

Homogeneity is determined by analyzing multiple samples of the same batch. If coating is homogenous, replicate samples will have essentially the same concentration and will there ore have a small relative standard deviation (% RSD) (preferably <2%, but the present disclosure should cover up to 20% or so). Therefore, analysis of replicate samples of the same batch (sample size 500 mg) shows 0-20% relative standard deviation (RSD). In embodiments, the relative standard deviation (RSD) is less than less than 25% less than 20%, less than 15%, less than 10%, less than 8%, less than 6%, less than 4%, less than 2%, less than 1%, less than 0.5%, and so on. In exclusionary embodiments, the present disclosure can exclude any composition, mixture, powder, coated powder, where relative standard deviation (RSD) is not less than 30%, not less than 25%, not less than 20%, not less than 15%, not less than 10%, not less than 8%, not less than 6%, not less than 4%, not less than 2%, not less than 1%, not less than 0.5%, and so on.

Relative standard deviation (RSD) is expressed in percent and is obtained by multiplying the standard deviation by 100 and dividing this product by the average, relative standard deviation, RSD [100] [SD]/average. The average is calculated by summing the individual results and dividing this sum by the number (n) of individual values, as shown by this formula: Average=[xr+x2+x3+x4+ . . . ]/n.

It is preferred that homogeneity in coating the powder is maximized. Also, it is preferred to maximize loading, that is, to have maximal amount of extract per gram of powder (gram of powder prior to loading), to have maximal amount of cannabinoid per gram of powder (gram of powder prior to loading), or to have maximal amount of non-cannabinoid compounds or chemicals per gram of powder (gram of powder prior to loading). In a preferred embodiment, homogeneity in coating and loading are both maximized.

Tablets with high doses will require very concentrated input powders and concentrated premade drink powders will require the same. Insufflatable powders will also require very high loading. A most preferred range would be 0-25%. An acceptable range is 0.01%-45%. Minimum useful loading is 0.01%, without implying any limitation. It is preferred to have no upper boundary. A preferred embodiment is a powder with turn particle size with 25% loading. The present disclosure provides powders, compositions of powders, related, methods, and such that comprise an "insufflatable powder." An insufflatable powder is a dry substance that is introduced into the human body via nasal passages, typically in conjunction with inhalation.

The present disclosure provides embodiments, as well as exclusionary embodiments, as set forth in U.S. Pat. Application No. 2015/0080265 of Elzinga and Raber, which is incorporated herein in its entirety.

Reducing or Eliminating Risk of Explosions.

The method reduces explosion risk by one or more of: (a) Limiting the plurality of edible particles to a mass of 10 kg or less, 5 kg or less, 2 kg or less, 1 kg or less, 750 grams or less, 500 grams or less, 250 grams or less, 100 grams or less, 50 grams or less, and so on; (b) Providing a ventilator that removes any dust by way of ventilation: (c) Limiting or not using any compounds that generate hydroxymethylfurfaral; (d) Limiting or eliminating flammable solvents; and (c) Limiting or eliminating use of elevated temperatures that can ignite a flammable solvent. To provide background information, dust may be defined as particles of 300 micrometers or less that are suspended in air. As surface area increases, the exposure of the dust matrix to atmospheric oxygen increases, with a resulting increase in risk for combustion when a spark is present. Granulated sugar is 570-635 micrometers in diameter, and powdered sugar is about 600 micrometers in diameter. Heat can induce sucrose to decompose and form a volatile chemical (hydroxymethylfurfural) which easily ignites (see, Tinnesand M (December 2010) Sugar an unusual explosive. ChemMatters; ScienceLab.com. Material Safety Data Sheet. 5-Hydroxy-2-Furaldehyde. Sciencelab.com, Inc., Houston, Tex.).

EXAMPLES

Example 1

To make 100 grams of greater than 10% THC coated powdered sugar: 87 grams of powdered sugar is added to a 300 ml polypropylene container with rounded corners and an impression is made into the center. 13 grams of warm liquid cannabinoids (containing approximately 80% THC) is poured into the impression so as to not touch the sides of the container. A lid is screwed onto the container and the container placed in a refrigerator at −20 degrees C. to harden the cannabinoids. Cover the top of the lump of cannabinoids with powder in the container to ensure it's completely covered. The chilled container is placed in the Dual Asymmetrical Centrifuge (DAC) and run at 2000 rpm for 90 seconds. After 90 seconds the container is checked for visual homogeneity. If a blob of cannabinoids still remains the container is run at 2000 rpm for 15 seconds. 15 second intervals are repeated until the powder is homogeneous. The temperature is checked after every run. If the temperature of the cup exceeds 50 degrees C. the container is allowed to cool to room temperature before further homogenization.

The cannabinoids preferably contains about 80% THC. Alternatively, the cannabinoids contains about 50% THC, about 55% THC, about 60% THC, about 65% THC, about 70% THC, about 75% THC, about 85% TUC, about 90% THC, about 95% THC about 100% THC, or any range of these concentrations, such as about 75% THC to about 85% THC.

The number of repeated DAC runs can be, for example, 2 repeats, 3 repeats, 4 repeats, 5 repeats, 6 repeats, 7 repeats, 8 repeats, 9 repeats, 10 repeats, 15 repeats, 20 repeats, and so on. The number of repeated DAC runs can be at least 2 repeats, at least 3 repeats, at least 4 repeats, at least 5 repeats, at least 6 repeats, at least 7 repeats, at least 8 repeats, at least 9 repeats, at least 10 repeats, at least 15 repeats, at least 20 repeats, and so on. Also, the number of repeated DAC runs can be not more than 2 repeats, not more than 3 repeats, not more than 4 repeats, not more than 5 repeats, not more than 6 repeats, not more than 7 repeats, not more than 8 repeats, not more than 9 repeats, not more than 10 repeats, not more than 15 repeats, not more than 20 repeats, and so on. The duration of the initial DAC run, of any repeat DAC run, or of both the initial and repeat DAC runs, can be 5 sec, 10 sec, 15 sec. 20 see. 30 sec, 40 sec, 50 see, 60 sec, 70 see, 80 see, 90 sec, 2 min, 3 min, 4 min, 5 min, and the like. Also, the duration be about 5 sec, about 10 sec, about 15 sec, about 20 sec, about 30 sec, about 40 see about 50 sec, about 60 see, about 70 sec, about 80 sec, about 90 see, about 2 min, about 3 min, about 4 min, about 5 min, and the like.

Example 2

To make 10 grains of saponin/THC paste: Add 5 grams of saponin powder to a 30 ml polypropylene cup and make a crater in the middle. Pour 5 grams of 80% THC liquid cannabinoids into the impression being careful to not let any touch the sides of the container. Immediately begin mixing at 2500 rpm for 120 seconds. After this time check the container for visual homogeneity and continuing mixing at 15 second pulses at 2500 rpm until homogeneous.

In paste embodiments, the disclosure provides paste that contains a ratio of [emulsifier]/[cannabinoid] of 5 grams/5 grams, 5.5 grams/4.5 grams 6 grams/4 grams, 6.5 grams/3.5 grams, 7 grams/3 grams, and so on. Also provided is a paste that contains a ratio of [emulsifier]/[cannabinoid] of 4.5 grams/5.5 grams, 4 grams/6 grams, 3.5 grams/6.5 grams, 3 grams/7 grams, and so on.

Example 3

Table 1 discloses reproducibility of analysis of a coated powder. The coating was THC, and the powder was powdered sugar. The left grouping checks the accuracy and precision of the analytical method used. The right grouping is the sample standard deviation (SD) for a % powdered sugar. Sample mass was the mass of the sample used for analysis and that is a sum of powder and cannabinoids. The sample standard deviation reasonably concluded as being below 0.05.

TABLE 1

Sample Standard deviation of THC (mg) per gram of coated powdered sugar particles

| Sample | Vial lid sticker (grams) | Vial lid sticker 10 mL ethyl acetate (EA) (grams) | Ethyl acetate (EA) (grams) | Sample mass | THC (mg)/ [gram of powder + cannabinoids] |
|---|---|---|---|---|---|
| 1 | 16.04541 | 25.01155 | 8.96614 | 1.00005 | 1.062 |
| 2 | 16.04056 | 25.00651 | 8.96595 | 1.00123 | 1.063 |
| 3 | 16.14637 | 25.11333 | 8.96696 | 1.00077 | 1.032 |
| 4 | 16.30244 | 25.26934 | 8.96690 | 0.99816 | 1.163 |
| 5 | 16.05985 | 25.02135 | 8.96150 | 1.0001 | 0.994 |
| 6 | 16.09826 | 25.06281 | 8.96455 | 0.9999 | 1.009 |
| 7 | 16.06243 | 25.01618 | 8.95375 | 1.00164 | 1.031 |
| 8 | 16.99146 | 24.9446 | 8.95314 | 1.00132 | 0.996 |
| 9 | 16.14369 | 25.10391 | 8.96022 | 1.0014 | 1.006 |
| 10 | 16.02856 | 24.9846 | 8.95604 | 1.00301 | 0.950 |
| | | | average 8.96152 | | |
| | | | Sample standard deviation 0.00549 | 0.001300443 | 0.035698 |

Physical Characteristics of Compositions Subjected to Homogenization

In some circumstances, a cannabinoid mass that has disintegrated into small pellets may resist homogenization. When a large ball of cannabinoids has its viscosity reduced too low it has been found to string out into small 1-3 mm spheres and it resists blending down further. Tests with refreezing have shown that even if the powder is refreezed, the small spheres of cannabinoids resist homogenization.

Loading Chemicals on Particles and Powders

Loading as high as 15% can be attained. In detail, this means that 15 g of cannabis extract can be coated onto 85 g powder to yield 100 gram of end product. This value was determined using confectioners' sugar which has a particle size of approximately 10-50 um. As this is a coating mechanism, higher loadings can be possible with smaller particle sizes as there is more surface area available.

It is to be understood that the present invention is not to be limited by compositions, reagents, methods, diagnostics, laboratory data, and the like, of the present disclosure, and that the present invention is not be limited by any preferred embodiments that are disclosed herein.

While several embodiments of the present disclosure have been describe and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof, and it is recognized that various modifications are possible within the scope of the claims. Accordingly, the claims are intended to cover all such equivalents.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrow or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As one skilled in the art would recognize as necessary or best-suited for performance of the methods of the invention, a computer system or machines of the invention include one or more processors (e.g. a central processing unit (CPU) a graphics processing unit (GPU) or both), a main memory and a static memory, which communicate with each other via a bus.

A processor may be provided by one or more processors including, for example, one or more of a single core or multi-core processor (e.g., AMD Phenom II X2, Intel Core Duo, AMD Phenom II X4, Intel Core i5, Intel Core I & Extreme Edition 980X, or Intel Xeon E7-2820).

An 1/0 mechanism may include a video display unit (e.g., a liquid crystal display (LCD) or a cathode ray tube (CRT)), au alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD) and Hash memory devices e.g., SD, micro SD, SDXC, SDIO, SDHC cards); magnetic disks, (e.g., internal hard disks or removable disks); and optical disks (e.g., CD and DVD disks).

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation alternative configurations of the present invention may be utilized in accordance with the teachings herein. Accordingly, the present invention is not limited to that precisely as shown and described.

What is claimed is:

1. A method for preparing a composition that comprises a plurality of coated particles, the method comprising the steps of:
   (i) Placing a plurality of edible particles it a container, wherein the container comprises a bottom and a retaining wall or sides,
      wherein the plurality of edible particles in the container is capable of receiving and supporting an added cannabinoid extract or resin and the plurality of edible particles is capable of substantially preventing contact of the cannabinoid extract or resin with the bottom of the container and is also capable of substantially preventing contact of the cannabinoid extract or resin with the retaining wall or sides,
   (ii) Placing a cannabinoid extract or resin on top of the plurality of edible particles, wherein the cannabinoid extract or resin does not substantially contact the bottom of the container, and does not substantially contact the retaining wall or sides of the container, and
   (iii) Mixing in a mixer until the cannabinoid extract or resin is substantially adsorbed to the surface of the edible particles to produce a primary coating, resulting in a composition of homogeneously coated edible particles, and wherein the homogeneously coated edible particles possess a homogeneity, wherein the homogeneity is definable by the range of values for a specific surface area in a sample of at least 1000 coated particles, or wherein the homogeneity is definable by the range values for ((mass of coating)/(mass of coated particles)) in a given sample of at least 1000 coated particles, wherein the method comprises one or more of: (a) active cooling during the process, (b) precooling the container, and (c) precooling the mixer.

2. The method of claim 1, wherein the mixing comprises device-mediated mixing.

3. The method of claim 1, wherein at the step where the cannabinoid extract or resin is placed on top of the plurality of edible particles, less than 10% of the extract or resin at this step contacts the bottom of the container, retaining wall, or sides.

4. The method of claim 1, wherein the container is an integral part of a mixer.

5. The method of claim 1, wherein the container is not an integral part of a mixer.

6. The method of claim 1, wherein the container has one or more internal sides and wherein the one or more internal sides of the container comprises discrete retaining walls, discrete sides, of a tubular retaining wall.

7. The method of claim 2, wherein the device-mediated mixing is with a dual asymmetrical centrifuge (DAC) mixer.

8. The method of claim 2, wherein the device-mediated mixing is with a DAC mixer, ribbon blender, kitchen blender, V-type blender, double cone blender, fluidized bed mixer, or mass mixer, or with any combination thereof.

9. The method of claim 2, wherein the device-mediate mixing is not with a mixer other than a DAC mixer.

10. The method of claim 1, wherein the method comprises applying an additional coating.

11. The method of claim 1, wherein the method comprises applying an additional coating and where the product is configured for eating as is, or is configured for combining with a food prior to cooking followed by cooking the combination of the product and the food.

12. The method of claim 1, wherein the plurality of coated particles comprises coated sugar particles, coated flour particles, or coated salt particles, or any combination thereof.

13. The method of claim 1, farther comprising coating the particle with one or more of a secondary coating substance, wherein the secondary coating substance is an emulsifier, pigment, or odorant, wherein coating the particle with the secondary coating substance can be prior to, after, or simultaneously with coating the particle with the primary coating substance.

14. The method of claim 1 that produces an edible product ha s capable of use as an ingredient for the preparation of a cooked food.

15. The method f claim 1 that produces a dry instant powder for use in adding to or mixing with water and making a flavored drink.

16. The method of claim 1 that produces a dry instant powder for use in adding to or mixing with water and making a medicated drink.

17. The method of claim 1, wherein the edible tides are comprised of one or more of a sugar, non-sugar sweeter, a salt, or a protein.

18. The method of claim 1, further comprising adding one or more of an emulsifier, a pigment, a flavoring compound, or a pharmaceutical, to the plurality of edible particles.

19. The method of claim 1, further comprising adding one or more of an emulsifier, a pigment, a flavoring compound, or a pharmaceutical, to the plurality of edible particles prior to initiating mixing.

20. The method of claim 1, further comprising adding one or more of an emulsifier, a pigment, a flavoring compound, or a pharmaceutical, to the plurality of edible particles during the mixing.

21. The method of claim 1 wherein the mixing comprises the step of manual mixing followed by device-mediated mixing.

22. The method of claim 1 wherein the method is characterized by reduced explosion risk from explosions originating from dust, wherein the reduced explosion risk is provided by one or more of:
  (a) Limiting the plurality of edible particles to a mass of 100 grams or less;
  (b) Providing a ventilator that removes dust by way of ventilation;
  (c) Limiting or not using any compounds that generate hydroxymethylfurfural;
  (d) Limiting or eliminating flammable solvents; or
  (e) Limiting or eliminating use of elevated temperature s that can ignite a flammable solvent.

23. The method of claim 1, wherein the plurality of edible particles consists of powdered sugar, wherein the homogeneously coated edible particles has a coated particle mass (grams), and wherein the plurality of edible particles has a mass of 87% the coated particle mass and the cannabinoid extract or resin has a mass of 13% the coated panicle mass.

24. A composition of coated particles produced by the method of claim 1, wherein the coated particles further comprise one or more of a secondary coating substance, wherein the secondary coating substance is an emulsifier, pigment, or odorant, wherein coating the particle with the secondary coating substance can be prior to, after or simultaneously with coating the particle with the primary coating substance.

25. An insufflatable powder comprising a composition of coated particles produced by the method of claim 1, wherein the coated particles further comprise one or more of a secondary coating substance, wherein the secondary coating substance is an emulsifier, pigment, or odorant, wherein coating the particle with the secondary coating substance can be prior to, after or simultaneously with coating the particle with the primary coating substance.

26. A confection or candy comprising a composition of coated particles produced by the method of claim 1, wherein the coated particles further comprise one or more of a secondary coating substance, wherein the secondary coating substance is an emulsifier, pigment, or odorant, wherein coating the particle with the secondary coating substance can be prior to, after or simultaneously with coating the particle with the primary coating substance.

27. A dry premix for making a beverage, wherein the dry premix comprises a composition of coated particles produced by the method of claim 1, wherein the coated particles further comprise one or more of a secondary coating substance, wherein the secondary coating substance is an emulsifier, pigment, or odorant, wherein coating the particle with the secondary coating substance can be prior to, after or simultaneously with coating the particle with the primary coating substance.

28. A method for preparing a composition that comprises a plurality of coated particles, the method comprising the steps of:
  (i) Placing a plurality of edible particles in a container, wherein the container comprises a bottom and a retaining wall or sides, wherein the plurality of edible particles in the container is capable of receiving and supporting an added cannabinoid extract or resin and the plurality of edible particles is capable of substantially preventing contact of the cannabinoid extract or resin with the bottom of the container and is also capable of substantially preventing contact of the cannabinoid extract or resin with the retaining wall or sides,
  (ii) Placing a composition comprising a cannabinoid extract or resin on top of the plurality of edible particles, wherein the cannabinoid extract or resin does not substantially contact the bottom of the container, and does not substantially contact the retaining wall or sides of the container, and
  (iii) Mixing in a mixer until the cannabinoid extract or resin is substantially adsorbed to the surface of the edible particles to produce a coating, resulting in a composition of homogeneously coated edible particles, and wherein the homogeneously coated edible particles possess a homogeneity, wherein the method comprises one or more of: (a) active cooling during the mixing process, (b) precooling the container, and (c) precooling the mixer.

29. The method of claim 28, wherein the composition comprising a cannabinoid extract or resin further comprises an emulsifier, and wherein the composition is a paste.

30. The method of claim 28, wherein the composition comprising a cannabinoid extract or resin further comprises saponin emulsifier, and wherein the composition is a paste.

31. The method of claim 1, wherein the active cooling or the precooling at about −5 degrees C., −10 degrees C., −15 degrees C., −20 degrees C., −25 degrees C., −30 degrees C., −40 degrees C., or −78 degrees C.

32. The method of claim 1, wherein each of the edible particles has a diameter in the range of 570-645 micrometers.

33. A composition of coated particles produced by the method of claim 1, wherein the edible particles are sucrose.

34. The composition of claim 33, wherein the sucrose is powdered sucrose or granulated sucrose.

* * * * *